(12) United States Patent
Zanca et al.

(10) Patent No.: US 10,786,222 B2
(45) Date of Patent: Sep. 29, 2020

(54) METHODS, SYSTEMS, AND APPARATUS FOR AUTOMATICALLY ASSESSING QUALITY OF IMAGING SYSTEMS

(71) Applicant: General Electric Company, Schenectady, NY (US)

(72) Inventors: Federica Zanca, Diegem (BE); Maxime Armbruster, Strasbourg (FR); Nicolas Grussenmeyer, Bischwiller (FR); Pierre Guntzer, Strasbourg (FR)

(73) Assignee: General Electric Company, Schenectady, NY (US)

( * ) Notice: Subject to any disclaimer, the term of this patent is extended or adjusted under 35 U.S.C. 154(b) by 359 days.

(21) Appl. No.: 15/827,833

(22) Filed: Nov. 30, 2017

(65) Prior Publication Data

US 2019/0159747 A1    May 30, 2019

(51) Int. Cl.
| | |
|---|---|
| *A61B 6/00* | (2006.01) |
| *G06T 7/00* | (2017.01) |
| *A61B 6/03* | (2006.01) |
| *G16H 30/40* | (2018.01) |
| *G01R 33/00* | (2006.01) |
| *G16H 40/40* | (2018.01) |
| *G16H 40/63* | (2018.01) |
| *G16H 30/20* | (2018.01) |
| *A61B 5/055* | (2006.01) |

(52) U.S. Cl.
CPC ............ *A61B 6/583* (2013.01); *G01R 33/007* (2013.01); *G06T 7/0016* (2013.01); *G16H 30/20* (2018.01); *G16H 30/40* (2018.01); *G16H 40/40* (2018.01); *G16H 40/63* (2018.01); *A61B 5/055* (2013.01); *A61B 2576/00* (2013.01)

(58) Field of Classification Search
CPC .. A61B 6/032; A61B 6/03; A61B 6/58; A61B 6/581; A61B 6/582; A61B 6/52; G06F 16/50
See application file for complete search history.

(56) References Cited

U.S. PATENT DOCUMENTS

| | | |
|---|---|---|
| 2006/0274145 A1 | 12/2006 | Reiner |
| 2009/0169088 A1 | 7/2009 | Bohm et al. |
| 2013/0268285 A1 | 10/2013 | Backes et al. |
| 2015/0157880 A1 | 6/2015 | Dalbow et al. |
| 2018/0096477 A1* | 4/2018 | Avila .................. G06T 7/0002 |

* cited by examiner

*Primary Examiner* — Don K Wong
(74) *Attorney, Agent, or Firm* — Hanley, Flight & Zimmerman, LLC

(57) ABSTRACT

Methods and apparatus for automatically assessing quality of imaging systems are disclosed. An example apparatus includes a processor configured to receive data from an imaging device; determine whether the received data corresponds to a test exam; in response to determining that the received data corresponds to the test exam, determine whether the test exam was correctly performed based on a comparison of the data to a validity criterion; and when the test exam was correctly performed, determine that the imaging system satisfies a performance criteria based on a comparison of a characteristic of the data corresponding to the performance indicator with a performance threshold; and a storage configured to store the performance indicator in conjunction with the data.

20 Claims, 7 Drawing Sheets

METHODS, SYSTEMS, AND APPARATUS FOR AUTOMATICALLY ASSESSING QUALITY OF IMAGING SYSTEMS

FIELD OF THE DISCLOSURE

This disclosure relates generally to medical imaging systems, and, more particularly, to methods, systems, and apparatus for automatically assessing quality of imaging systems.

BACKGROUND

Components of imaging devices can age over time to affect quality of images captured by such imaging device (e.g., x-ray, computed tomography (CT), magnetic resonance (MR), radio waves, etc.). An emitter within the cathode emits a stream of electrons in response to heat resulting from an applied electrical current, and/or an electric field resulting from an applied voltage to a properly shaped metallic plate in front of the emitter. The anode includes a target that is impacted by the stream of electrons. The target, as a result of impact by the electron beam, produces x-ray radiation to be emitted toward an imaged volume. In such imaging systems, a portion of the radiation passes through a subject of interest, such as a patient, baggage, or an article of manufacture, and impacts a digital detector or a photographic plate where the data set is collected. The signals are then processed to generate an image that may be displayed for review. In other systems, such as systems for oncological radiation treatment, a source of x-rays is used to direct ionizing radiation toward a target tissue. Other non-invasive imaging systems include magnetic resonance scanners using strong magnetic fields, radio waves, and field gradients to generate images of a subject.

Today in medical imaging, medical physicist experts (MPEs) perform Quality Control tests (e.g., after equipment acceptance test at installation) to ensure a correct operating of an imaging device. For example, an MPE may perform a first acceptance test to define a baseline of performance indicator values and then may follow up with an annual quality control test to benchmark updated values with the values of the baseline acceptance test. These tests are time quite time consuming. Accordingly, such tests are performed annually or biannually. There are certain system parameters for which an annual test is sufficient. There are others which should be tested everyday (e.g., screening systems in mammography) or to see if an x-ray tube is going to fail, ensuring that you have a spare part before the x-ray tube fails. In the field of medical imaging (e.g., CT scanning, mammographs, X-ray, MM, radio, interventional, etc.) test exams are performed and the results are analyzed by a technician/physicist in the hospital and/or are outsourced to determine if the performance of the imaging device is acceptable (e.g., based on key performance indicators (KPIs)).

To ensure that such imaging systems are properly functioning, quality assurance programs are regularly performed (e.g., on a yearly, monthly, weekly, and/or daily basis, depending on the modality and on the device utilization). Quality assurance (QA) is the overarching program that determines if operators are using imaging devices correctly. A subset of QA is quality control (QC) that determines if the imaging devices are operating correctly. Thus, QC is an ongoing, periodic evaluation procedure to detect changes that may result in a clinically significant degradation in image quality or a significant increase in radiation exposure. Certainly, optimal QA requires optimal QC, but often overlooked is the human element, since imperfect operation of a technically optimal system will result in substandard image outcomes. Continuous quality improvement is a factor for acting on QA and QC findings to strive for optimal patient care.

BRIEF SUMMARY

Certain examples provide an apparatus for automatically assessing quality of imaging systems. The example apparatus includes a processor configured to receive data from an imaging device, determine whether the received data corresponds to a test exam, in response to determining that the received data corresponds to the test exam, determine whether the test exam was correctly performed based on a comparison of the data to a validity criterion, and, when the test exam was correctly performed, determine that the imaging system satisfies a performance criteria based on a comparison of a characteristic of the data corresponding to the performance indicator with a performance threshold. The example apparatus further includes a storage configured to store the performance indicator in conjunction with the data.

Certain examples provide a method for automatically assessing quality of imaging systems. The example method includes receiving data from an imaging device. The example method further includes determining whether the received data corresponds to a test exam. The example method further includes, in response to determining that the received data corresponds to the test exam, determining whether the test exam was correctly performed based on a comparison of the data to a validity criterion. The example method further includes, when the test exam was correctly performed, determining that the imaging satisfies a performance criteria based on a comparison of a characteristic of the data corresponding to the performance indicator to the data with a performance threshold. The example method further includes storing the performance indicator in conjunction with the data.

Certain examples provide a computer readable storage medium comprising instructions which, when executed, cause a machine to receive data from an imaging device. The example instructions further cause the machine to determine whether the received data corresponds to a test exam. The example instructions further cause the machine to, in response to determining that the received data corresponds to the test exam, determine whether the test exam was correctly performed based on a comparison of the data to a validity criterion. The example instructions further cause the machine to, when the test exam was correctly performed, determine that the imaging satisfies a performance criteria based on a comparison of a characteristic of the data corresponding to the performance indicator to the data with a performance threshold. The example instructions further cause the machine to store the performance indicator in conjunction with the data.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
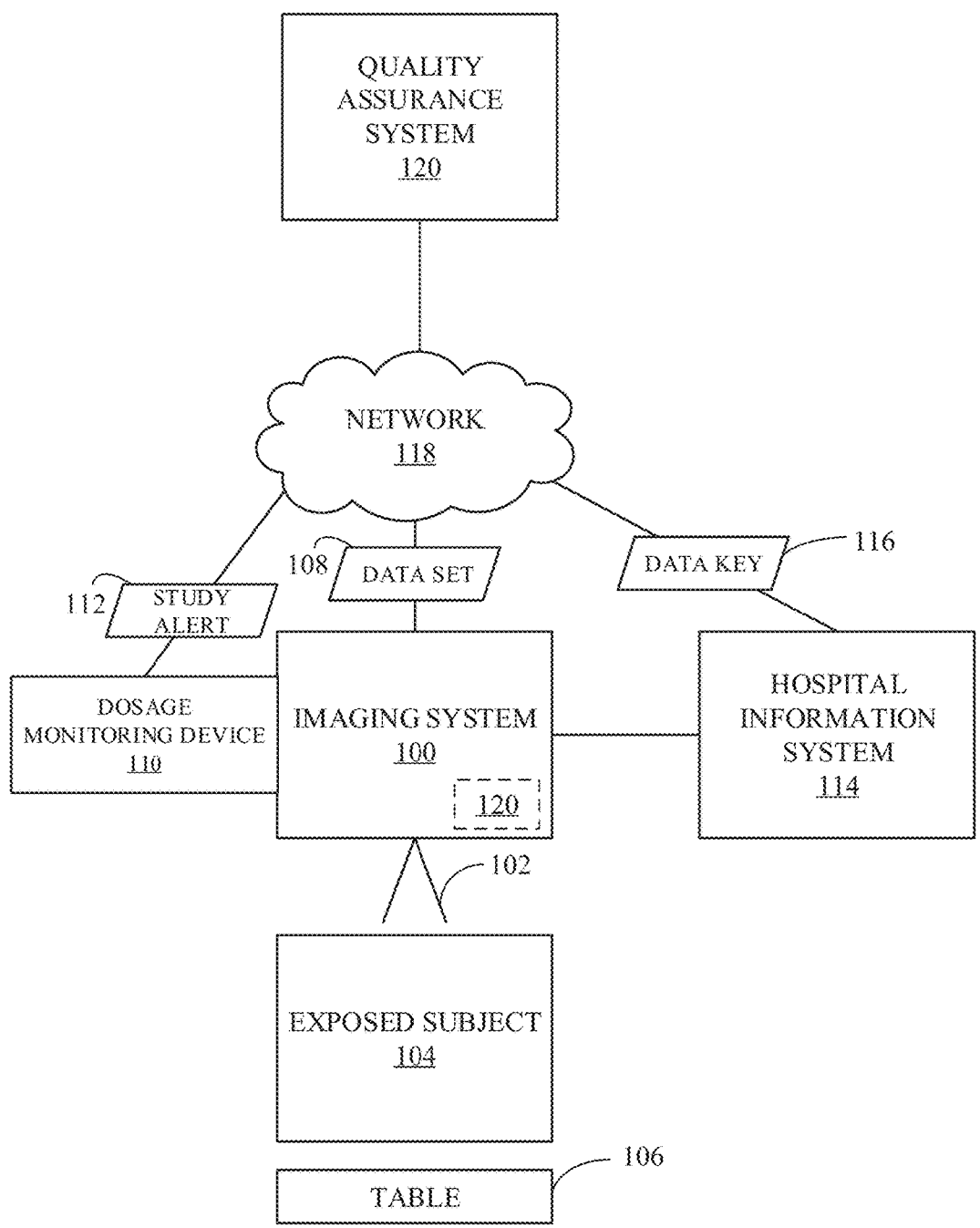
FIG. 1 is an illustration of an example environment for automatically assessing quality of imaging systems.

In the field of imaging devices (e.g., magnetic resonance imaging (MRI) devices, X-Ray scanning devices used for computed tomography (CT) scanning, mammography scanning, etc.), most hospitals have a quality assurance policy in place to ensure that such imaging devices are properly functioning. For example, to determine if an imaging device is properly functioning, the imaging device performs a test exam on a phantom (e.g., an object made with various quantities of x-ray contrast agents with certain x-ray absorbing qualities) with known characteristics. Because the characteristics of the phantom are known, the resulting test exam data set (e.g., a digital imaging and communications in medicine (DICOM) image) is compared to the known phantom characteristics to determine one or more performance indicators of the image scanning device. As another example, dose report or computerized maintenance management system (CMMS) maintenance logs can be examined to determine whether an imaging device is properly functioning.

Analyzation of test exams by technician to determine performance of an imaging device is expensive and measurements are not stored anywhere to observe trends over time. Additionally, the list of key performance indicators (KPIs) is not shared between hospitals using the same device. Accordingly, there is no traceability (e.g., among KPIs and/or for the same KPI across multiple imaging devices and/or hospitals) in a database and no way to observe evolutions in performance indicators over time. Additionally, there is no automatic notification to a hospital that a particular performance indicator is outside of a predefined limit or if a test exam is needed (e.g., a test exam has not been performed within a preset amount of time/number of scans). Accordingly, there is no indication that a patient scan includes inaccurate information because a performance indicator has not been met and/or a test scan has not been performed within the preset amount of time/number of scans. Examples disclosed herein include an integrated system that solves the above problems by implementing an integrated system in a hospital information system that automatically analyzes test exams and stores results to provide (e.g., generate) reports based on imaging device functionality over time. Examples disclosed herein can be configured to adapt to the hospital information system and can be designed to be integrated in the daily usage of a hospital department that utilizes imaging systems (e.g., a radiology department, a cardiology department, etc.).

According to the present disclosure, one method of reducing the cost and lack of information of conventional imaging system performance analysis includes a system to track performance of imaging devices on a daily basis, for example, such a system includes a device to gather data set generated by scanning devices and process the data set to determine if the data set corresponds to a test exam (e.g., a scan of a known object of phantom for device testing purposes) or a patient exam (e.g., a scan/image of a patient or part of the anatomy of the patent). For example, the system can process metadata of the image based on a data key from a hospital information system to determine that the image is a test image. Once the system determines that the image corresponds to a test exam, the system processes the test exam image to verify that validity of the test exam image. For example, if the test exam image implies a specific phantom, the phantom can be required to be positioned in a predefined position. If the position of the test exam image is incorrect, the system tags the image as invalid. In some examples, the data set may include multiple images. In such examples, the system may process the multiple images to determine the validity of the multiple images. Additionally or alternatively, the system can determine validity of a test exam image based on shifts from the isocenter, difference in the levels of grey between to side of the image, etc.

When the system determines that the test exam image is valid, the system measures relevant performance indicators (e.g., KPIs) of the data set, set forth by a user, a hospital, and/or medical regulations. Relevant performance indicators correspond to indicators that are relevant to imaging (e.g., indicators that correspond to the obtaining a high-quality image associated with obtaining a diagnosis for a disease with a low dose with an x-ray is used). Additionally or alternatively, relevant performance indicators may correspond to indicators that correspond to possible malfunctions of the system. For example, because parts of an imaging system is very stable and other parts are less stable, relevant performance indicators may correspond to the unstable parts (e.g., tube current, detector response, homogeneity, etc.). Each performance indicator corresponds medical to an acceptable threshold range of values defined by the user, hospital, and/or national/international standards/guidelines. A measured performance indicator value being within a corresponding threshold range of values corresponds to an acceptable scanning device, while a measured performance indicator value being outside a corresponding range of values correspond to an unacceptable scanning device. Accordingly, the system triggers an alert when one or more of the measured performance indicator values is outside of a corresponding threshold range of values. Additionally, the system stores the measured performance indicator values in storage (e.g., a database). In this manner, the system can output a report identifying trends of the performance indicator measurements in time, based on device, location, etc. In addition to using relevant key performance indicators for a daily quality control test, examples disclosed herein identify one or more phantoms that may or may not be modality specific and that are sensitive enough to allow the measurements of relevant performance indicators, for the specific modality and/or clinical indication. Accordingly, examples disclosed herein may select a phantom which is specific for the number of relevant performance indicators that may be measured based on the phantom. With that in mind, a system to gather scanning data set and (A) identify if the data set correspond to test exams, (B) determine the validity of the test exams, and (C) determine functionality of the scanning device based on measured performance indicators on the validated data set will provide fuller information corresponding to scanning devices (e.g., trends over time) and eliminate the costs associated with daily device manually analyzing test exam images.

FIG. 1 illustrates an example environment for automatically assessing quality of imaging systems. As illustrated in FIG. 1, in some embodiments, the environment includes an imaging system 100, a data set 108, a dosage monitoring device 110, a study alert 112, a hospital information system 114, a data key 116, a network 118, and a quality assurance system 120. Although the quality assurance system 120 can be located remote from the imaging system 100 of FIG. 1, the quality assurance system 120 can otherwise be integrated with or located adjacent to the imaging system 100 of FIG. 1, as further described below.

The imaging system 100 can be any a device that captures one or more images of the subject. For example, the imaging system 100 can be an angiographic imaging system, a CT imaging system, a fluoroscopic imaging system, etc., having a radiation source projecting a beam of ionizing radiation (e.g., x-rays) toward a exposed subject. In another example, the imaging system 100 can be a magnetic imaging system, an MRI imaging system, having a magnetic source projecting the beam of magnetic waves, radio waves, and/or field gradients toward the exposed subject 104. The image(s) can display or illustrate a region of interest of the exposed subject. The imaging system 100 generates the data set 108 (e.g., DICOM data set, scout data set, etc.), as well as stores a scanning range associated with the data set 108, for communication to the quality assurance system 120 (e.g., via the network 118). In some examples, the data set 108 corresponds to an image of a phantom. In some examples the data set 108 corresponds to an image of a real patient. Additionally, the imaging system 100 can include metadata (e.g., a header or DICOM header tag) in the data set 108. The metadata can include a data set identifier (e.g., identifying the exposed subject, a data set type identifier (e.g., identifying what type of image(s) and/or portion of the exposed subject was captured), a phantom type (e.g., for test exams), information related to how the data set was obtained, etc. In some examples, the data set 108 may be diagnostic data. In some examples, the data set 108 can be a data set or a data structure(s) include multiple images generated by the imaging system 100. The protocol for including the information in the header/metadata can be defined by the hospital information system 114, as further described below. In some examples, the quality assurance system 120 is implemented in the imaging system 100, as further described below. In some examples the data set 108 may be data from filter ages, maintenance management systems (e.g., CMMS), etc.

In some examples, the dosage monitoring device 110 may be included to collect and analyze a beam or other image capturing device (e.g., radio waves, radiation, etc.) while the imaging device 100 is operating to help ensure that a patient and/or technician is not exposed to too much radiation (e.g., for a radiation based beam) while producing one or more high quality images. The dosage monitoring device 110 may operate within the imaging device 100 or may be connected to the imaging device 100 (e.g., via a wired or wireless connection). In some examples, the dosage monitoring device 100 receives the data set 108 from the imaging system 100 when the imaging system has performed a test exam. In such examples, the dosage monitoring device 100 processes the data set 108 and sends the example study alert 112 including an identifier of the data set 108 to the quality assurance system 120 (e.g., via the quality assurance system 120), the alert being triggered based on one or more predefined alert criteria (e.g., a characteristic corresponding to a performance indicator exceeding a predefined threshold).

The hospital information system 114 generates a worklist of all the patients to be imaged by the imaging system 100. For example, when a patient is registered to be scanned, the hospital information system 114 provides the patient information to the imaging system 100. In this manner, when a exposed subject (e.g., the patient) arrives to be imaged, a user or technician selects the patient from a user interface on the imaging system 100. When a test exam is to occur, the user or technician places the exposed subject (e.g., a phantom) to be imaged. For a test exam, the user or technician can (A) run the imaging system 100 without selected patient information and/or (B) identify that the test exam is a test exam on the user interface before initiating the test exam. Accordingly, the imaging system 100, when generating the data set 108, include information in the metadata identifying that the data set 108 corresponds to a test exam (e.g., by tagging the data set as a test exam or as an image not linked to a patient). The imaging system 100 includes the information based on a protocol set forth by the hospital information system 114. For example, the imaging system 100 can generate a preset identifier for a test exam or a preset identifier corresponding to an unknown patient. The hospital information system 114 generates the data key 116 based on the protocol set forth by the hospital information system and transmits the data key 116 to the quality assurance system 120 (e.g., via the network 118). Accordingly, the quality assurance system 120 can determine how to process the metadata of the data set 108 to determine if the data set 108 corresponds to a test exam. In some examples, the hospital information system 114 can include additional information in the data key 116. For example, the data key 116 can include information corresponding to how to process the metadata of the data set 108 to determine if the data set 108 corresponds to specific phantom type. In some examples, the data key 116 may include universal identifiers (UIDs) to reference a set of data sent by the imaging system 100.

The network 118 can facilitate transmission of electronic or digital data within and/or among the environment of FIG. 1. The network 118 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN), a local area network (LAN), the Internet, a cloud-based computing infrastructure of computers, routers, servers, gateways, etc., or any combination thereof that allows the quality assurance system 120 to communicate with the imaging system 100 and/or the hospital information system 114. With respect to the example implementation of the network 118 including a cloud-based infrastructure, components in the environment of FIG. 1 can share information via web-based applications, cloud storage and cloud services. For example, a Web-based portal can be used to facilitate access to information, etc. The Web-based portal can be a central interface to access information and applications, and data can be viewed through the Web-based portal or viewer, for example. Additionally, data can be manipulated and propagated using the Web-based portal, for example. The Web-based portal can be accessible locally (e.g., in an office, in an operating room, in a radiology reading room, etc.) and/or remotely (e.g., via the Internet and/or other network or connection), for example.

The quality assurance system 120 receives the data set 108 from the imaging system 100 and the data key 116 from the hospital information system 114 (e.g., via the network 118) to determine the performance of the imaging system 100 based on performance indicators. The quality assurance system 120 processes the data set 108 to determine if the received data set corresponds to a test exam (e.g., an image of a phantom with known (e.g., previously quantified, etc.) characteristics) rather than a patient exam, based on the data key 116. In some examples, the data key 116 can include information that informs the quality assurance system 120 as to how to process the data set 108 to determine whether the data set 108 is a test exam rather than a patient exam. For example, if the imaging system 100 includes a preset identifier in the metadata of data set corresponding to test exams, the data key 116 can include the preset identifier. In such an example, the quality assurance system 120 determines that the data set 108 corresponds to a test exam when the identifier listed in the data key 116 is within the metadata of the data set 108.

Once the quality assurance system 120 determines that the received data set 108 corresponds to a test exam, the quality assurance system 120 determines if the test exam was correctly performed based on the application of validity criteria on the data set 108. The validity criteria can correspond to, for example, shift between the isocenter of the device and the center of the phantom used for the test exam, differences in the levels of grey between two sides of the image, etc. The validity criteria can be general validity criteria and/or can be specific validity criteria corresponding to a phantom type. For example, if the test exam implies a specific phantom, a specific validity criterion can correspond to the position of the phantom with respect to an isocenter. Specific criteria can correspond to specific phantom types and/or data set types (e.g., mammography, CT, etc.). For example, if the data set 108 is a mammography data set, the validity criteria can correspond to field uniformity and/or automatic exposure control (AEC). In another example, if the data set 108 is a CT data set, the validity criteria can correspond to a specific phantom centering, a consistency of Hounsfield units, a tube current modulation, etc. When the specific criteria differs from the general criteria, the quality assurance system 120 utilizes the specific criteria. The data set type can be included in the metadata of the data set 108.

Once the quality assurance system 120 of FIG. 1 validates the test exam, the quality assurance system 120 measures the performance of the imaging system 100 by determining (e.g., measuring) a characteristic of the data set 108 corresponding to a performance indicator (e.g., KPI, etc.) and comparing the measured/determined characteristic to corresponding performance indicator threshold to determine if the imaging system 100 satisfies a predefined condition/performance criteria (e.g., a condition that sets the performance indicators and/or performance indicator thresholds). The quality assurance system 120 may determine the characteristic of the data set 108 corresponding to the performance indicator by processing the image(s) of the data set 108 and/or obtaining information stored in the metadata of the data set 108. A performance indicator corresponds to measurement parameters that are influenced by other fundamental metrics that affect the performance of the imaging system 100. In some examples, each performance indicator corresponds to a threshold that reflects a functional performance. A performance indicator can be based on, for example, Computed Tomography (CT) numbers, noise (e.g., the standard deviation of the Hounsfield units (HU) with a predefined return on investment, where HU is defined as $$1000 \frac{\mu - \mu_{water}}{\mu_{water}}$$

and $\mu$ is a linear attenuation coefficient), Uniformity (e.g., how invariable the image(s) of a homogenous material appears), tube current modulation, etc. For example, Table 1 illustrates an example list of general KPIs, how the KPIs are tested, and an acceptance range (e.g., when a measured KPI of a data set is acceptable/satisfied). Although, Table 1 includes example KPI values and acceptance ranges, other performance indicators may be added or removed and/or the acceptance ranges may be adjusted based on user and/or preferences.

TABLE 1

GENERAL PERFORMANCE INDICATORS

| KPI | KPI Test | Acceptance |
|---|---|---|
| CT number (IQ_HU_value) | \|HU in central region of interest ($ROI_{HU}$) – Base value $ROI_{HU}$\| | <10 HU [1-4] |
| Noise (IQ_noise) | 100 * \|Noise in central ROI – Base value noise\|/Base value noise | <20% [2] |
| Uniformity | \|HU in central $ROI_{HU}$ – HU in peripheral $ROI_{HU}$\| | <8 HU in 16 cm diameter phantom [2] <12 HU in 24 cm diamater phantom [2] |

In some examples, there can be specific performance indicators and/or performance indicator thresholds (e.g., acceptance ranges) for specific phantom types. Tables 2-3 illustrate specific performance indicators. For example, Table 2 corresponds to performance indicators and acceptance ranges corresponding to a conventional radiography (CR) phantom, and Table 3 corresponds to performance indicators and acceptance ranges corresponding to an interventional radiology (IR) phantom. Although. Tables 2-3 include example KPI values and acceptance ranges, other performance indicators may be added or removed and/or the acceptance ranges may be adjusted based on user and/or preferences.

TABLE 2

PERFORMANCE INDICATORS FOR CR TYPE PHANTOM

| KPI | KPI test | Acceptance |
|---|---|---|
| mAs consistency | 100 * \|mAs – Average mAs\|/Average mAs | <10% [12] |
| AEC | 100 * \|LEI – Average LEI\|/Average LEI | <20% [12] |

TABLE 2-continued

PERFORMANCE INDICATORS FOR CR TYPE PHANTOM

| KPI | KPI test | Acceptance |
| --- | --- | --- |
| LEI consistency | Variation in time | <10% [12] |
| Fluoroscopy Dose rate | Compare air kerma per unit of time to reference | <2 µGy/second (s) [14] |
| Homogeneity | Variance in a translating ROI of 2 mm × 2 mm is compared to all neighboring ROIs | <30% |
| Homogeneity (HomogeneityChange) | Change in time of Variance and SNR in $ROI_{ref}$ | <10% |
| Stability | Variance and SNR in $ROI_{ref}$ versus entire image | <15% |

TABLE 3

PERFORMANCE INDICATORS FOR INTERVENTIONAL TYPE PHANTOM

| KPI | KPI Test | Acceptance |
| --- | --- | --- |
| Standard fluoroscopy dose rate (FLU_STD_Doserate) | Compare air kinetic energy released per unit mass (kerma) per unit of time to reference | <2 µGy/s [14] |
| High dose fluoroscopy dose rate (FLU_CIN_Doserate) | Compare air kerma per unit of time to reference | <1.46 mGy/s [16] |
| Standard fluoroscopy dose rate consistency (FLU_STD_DoserateChange) | Variation in time | <20% reference <25% for entrance dose measurements in Belgian protocol |
| High dose fluoroscopy dose rate consistency (FLU_CIN_DoserateChange) | Variation in time | <20% reference |
| Record series Homogeneity (REC_Homogeneity) | Variance in a translating ROI of 2 mm × 2 mm is compared to all neighboring ROIs | <30% |
| Record series Homogeneity (REC_HomogeneityChange) | Change in time of Variance and SNR in $ROI_{ref}$ | <10% |
| Stability | Variance and SNR in $ROI_{ref}$ versus entire image | <15% |

Tables 1-3 include the performance indicator, a performance indicator test and an acceptance value/range. The performance indicator test corresponds to how to determine whether a characteristic of the data set 108 that corresponds to the performance indicator. The acceptance value/range is a performance indicator threshold value/range, thereby ensuring that a predefined condition is satisfied. The predefined condition is a standard that may be implemented by a technician, hospital, regulatory committee, etc. Accordingly, the quality assurance system 120 may analyze different performance indicators based on the different predefined conditions from any combination of different hospitals, technicians, regulatory committee, etc. Some of the information for the performance indicator test may be determined by processing one or more images of the data set 108 and other information may be determined by processing the metadata of the data set 108. As described above, although there may be multiple performance indicators, the quality assurance system 120 may only select relevant performance indicators to check on a daily based. For example, relevant performance indicators may correspond to unstable parts of the imaging system corresponding to possible malfunctions and/or indicators related to image quality and/or dosage. If the quality assurance system 120 has multiple phantoms for a particular imaging device, the example quality assurance system 120 may select a phantom based on the number of relevant performance indicators that may be determined based on the phantom. For example, if the quality assurance system 120 determines that a particular phantom corresponds to more possible performance indicators measurements than the other phantoms, the quality assurance system 120 selects the phantom for the QC test.

In some examples, the quality assurance system 120 can analyze data sets corresponding to real patient data. For example, if the data set 108 may correspond to an x-ray image of a real patient. In such an example, the quality assurance system 120 may select the x-ray image of the data set 108 to process a deviation index (e.g., a relevant performance indicator). A deviation index is a difference between an exposure index (e.g., a measure of the detector response to radiation in the relevant image region acquired with a digital x-ray imaging system as defined) and a target index (e.g., an expected exposure index when the detector is properly exposed, which can be disease dependent and fixed on a machine), thereby utilizing an automatic exposure control with patient specific data. In this manner, the quality assurance system 120 can track the DI as a function of disease, patient characteristics, etc., to determine the performance of the imaging device 100. In some examples, the quality assurance system 120 can analyze rejected images on real data. For example, if a subject undergoing a chest x-ray is not properly positioned, the technologist may reject (e.g., delete) the image and acquire a new image with better positioning which allows a doctor to better diagnose the subject. Although conventional systems do not track rejected images, rejected images contribute to the total radiation dose to a patient. Accordingly, tracking rejected images allows for assessing the correct dose delivered to a patient as well as opportunities for training of better machine utilization.

Additionally, the quality assurance system 120 can trigger one or more alerts based on one or more events. For example, the quality assurance system 120 can trigger an alert based on a threshold amount of time/scans without a test exam occurring, when a test exam was incorrectly performed, and/or when one or more measured performance indicator calculates is outside of a threshold range of values. The quality assurance system 120 stores the data set 108, the performance indicator measurements, and/or any other information (e.g., timestamp, identifiers, etc.) into one or more databases. The quality assurance system 120 provides reports corresponding to the performance of one or more imaging system over time based on the stored data. The quality assurance system 120 is further described below in conjunction with FIG. 2.

In some examples, when the quality assurance system 120 receives the study alert 112 corresponding to a notification that an example on a real patient has been performed, the quality assurance system 120 processes the study alert 112 to determine a data set identifier stored in the study alert 112. Once the data set identifier is identified, the quality assurance system 120 can obtain the corresponding data set from storage and process the corresponding data set to determine treatments and/or send notifications back to the dosage monitoring device 100 (e.g., via the network 118). For example, the quality assurance system 120 may compare the selected data set to achieved quality control data (e.g., corresponding to other data set stored in storage) to adjust parameters to try and/or adjust imaging system 100 settings and/or trigger alerts to notify an operator to an issue. For example, quality assurance system 120 may notify a user that an exam was performed on one or more patients while the corresponding modality did not successfully pass the daily QA test. In some examples, when the data set identified in the study alert 112 corresponds to a particular modality (e.g., Mammography, CT, etc.) and/or processing type (e.g., a field uniformity test and AEC, phantom centering, consistency of household units, tube current modulation, etc.). In such examples, the quality assurance system 120 may compare the identified data set to archived data corresponding to the modality and/or processing type.

As shown in the illustrated example of FIG. 1, the quality assurance system 120 can be a stand-alone device and/or can be implemented within the imaging system 100. When the imaging system 100 is implemented in the imaging system 100, the quality assurance system 120 can output real-time alerts to a technician. For example, if the technician has taken more than X scans without performing a test exam or it has been more than Y amount of time since the last test exam, the quality assurance system 120 can alert the technician that a test exam is required. In another example, if the technician takes a test exam that does not match the validity criteria, the quality assurance system 120 can alert the technician to the failure and/or reasons why the test exam failed.

Figure 2:
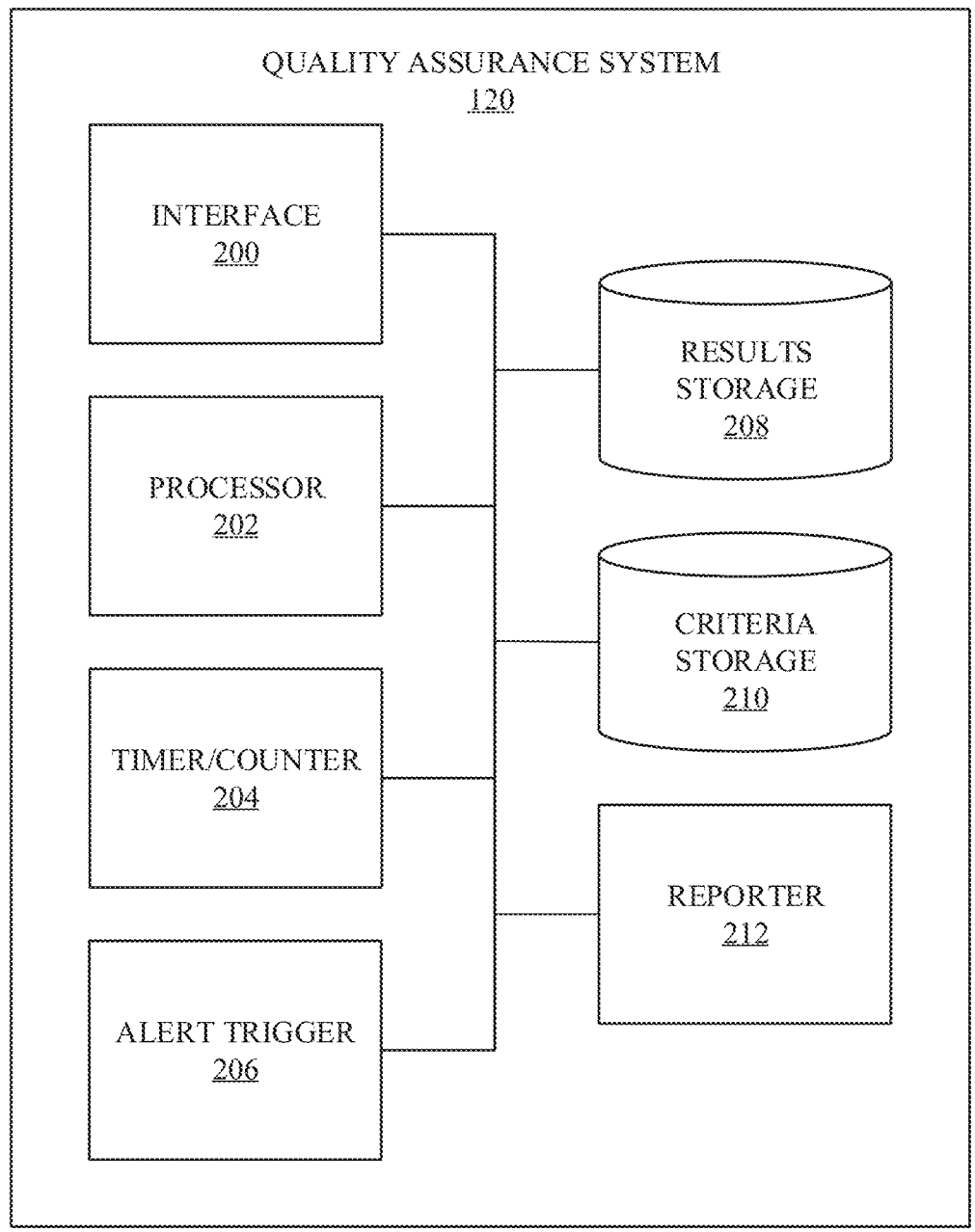
FIG. 2 is a block diagram of an example quality assurance system that can be used in the environment of FIG. 1.

FIG. 2 is a block diagram of an example implementation of the quality assurance system 120 of FIG. 1. The quality assurance system 120 of the example of FIG. 2 is configured to automatically assess quality of imaging systems. The quality assurance system 120 of FIG. 2 includes an interface 200, a processor 202, a timer/counter 204, an alert trigger 206, a results storage 208, a criteria storage 210, and a reporter 212.

The interface 200 receives the data set 108 from the imaging system 100 (e.g., via the network 118), the study alert 112 from the dosage monitoring system 110, and/or the data key 116 from the hospital information system 114 (e.g., via the network 118). In some examples, the interface 200 interfaces with a user to receive instructions regarding how the reporter 212 provides a report. In some examples, the interface 200 transmits alerts and/or reports to the hospital information system 114, the dosage monitoring device 110, and/or the imaging system 100. The interface 200 can include multiple interfaces to perform the different functions.

The processor 202 processes the received data set 108. In some examples, the data set 108 includes data of multiple images from the imaging system 100. In some examples, the processor 202 determines if the data set 108 corresponds to a test exam(s) by processing the metadata of the received data set 108. For example, the metadata may include an identifier or code that corresponds to a test image(s). Accordingly, the example data processor 202 may process the metadata of the data set 108 to determine is the test image identifier(s) is/are present. Different hospitals and/or imaging systems can identify the data set 108 as a test exam(s) using different techniques. Accordingly, the hospital information system 114 transmits the data key 116 that identifies how to process the metadata of the data set 108 to determine whether the data set 108 corresponds to a test exam(s). For example, the data key 116 includes which identifiers correspond to a test exam(s) and/or the location of an identifier frame in the metadata. In some examples, the processor 202 determines if a test exam(s) was correctly performed by analyzing the data set 108 based on validity criteria. The validity criteria can be, for example, a characteristic(s) of the data set 108, including shift from an isocenter, differences in the levels of grey between two sides of the image, field uniformity, AEC, phantom centering, consistency if Hounsfield units, Tube current modulation, etc. The processor 202 accesses the criteria database 210 to obtain the validity criteria. For example, when the data set 108 corresponds to a general data set, the processor 202 obtains general validity criteria from the criteria database 210. When the data set 108 corresponds to a specific data set (e.g., a mammography type, a Mill type, a CT type, etc.), the processor 202 obtains specific validity criteria corresponding to the phantom type and/or general validity criteria from the criteria database 210. General data set corresponds to data set associated with a phantom whose phantom type is unknown (e.g., not embedded in the metadata data of the data set file 108). Specific data set corresponds to data set associated with a phantom whose phantom type is known (e.g., embedded in the metadata of the data set 108. In some examples, the processor 202 gathers a data set from the results storage 208 corresponding to a phantom that is associated with the highest number of relevant performance indicators to perform a quality control test.

In some examples, the processor 202 measures relevant performance indicator value(s) (e.g., KPI value(s)) of the data set 108. A performance indicator can be based on, for example, computed tomography numbers, noise, uniformity, tube current modulation, etc. The relevant performance indicators and/or corresponding performance indicator thresholds can be based on hospital and/or national standards and can be adjusted with time. In some examples, the one or more performance indicators and/or performance indicator threshold values (e.g., corresponding to when the imaging system 100 is functional) can correspond to a phantom type. Example performance indicators and/or performance indicator threshold values are described above in conjunction with Tables 1-3. As described above, difference hospitals, countries, states, etc. may have different restrictions/regulations/performance criteria corresponding to different performance indicators. Accordingly, the example processor 202 may identify the relevant performance indicator values based on the one or more different performance criteria based on the location of the imaging device (e.g., specific instructions from a particular hospital).

The timer/counter 204 tracks time and/or a count to determine when the imaging system 100 should perform a test exam. For example, a hospital or a regulation can require a test exam after a predefined number of scans and/or after a predefined amount of time. In some examples, the timer/counter 204 can track when a preset period of time and/or other interval has passed. For example, a hospital or regulation can require a daily test exam. Accordingly, the timer/counter 204 can determine when a predefined point of time has passed to identify that a test exam should occur. In some examples, the quality assurance system 120 can include a timer and/or a counter as separate components.

The alert trigger 206 triggers an alert to identify potential problems/issues. In some examples, the alert trigger 206 can trigger an alert when a threshold number of exams and/or a threshold amount of time has occurred since the last test exam. In some examples, the alert trigger 206 can trigger an alert when a test exam was not correctly performed. In some examples, the alert trigger 206 can trigger an alert when one or more performance indicator values do not satisfy one or more corresponding threshold values (e.g., corresponding to performance of the imaging system 100). The alert trigger 206 can trigger alert that is transmitted to the hospital information system 114, the example dosage monitoring device 110, and/or the imaging system 100 (e.g., via the interface 200).

The results storage 208 stores the results of the analysis of a received data set 108. For example, the results storage 208 can store data in conjunction with the data set received from the imaging system 100. The image data can include the image, timestamps of when the image(s) was generated, measured performance indicator values of the image(s), any alerts that may have been triggered, any corresponding phantom types, data related to whether the image(s) was correctly performed, and/or any other data related to the image(s). The criteria storage 210 stores various criteria that can be used by the processor 202. For example, the criteria storage 210 can store performance indicators and corresponding threshold ranges, specific validity criteria, and/or general validity criteria. As described above in conjunction with FIG. 1, validity criteria may correspond to characteristic(s) of the data set 108, including a shift from an isocenter, differences in the levels of grey between two sides of the image(s), field uniformity values, AEC values, consistency of Hounsfield units, a tube current modulation, etc.

The reporter 212 provides reports based on the data stored in the results storage 208. The report can be customizable by a user. For example, the reporter 212 can provide a report based on the changes and/or comparisons of performance indicator values of one or more imaging systems within a defined duration of time. In some examples, the reporter 212 can transmit the report as data to another device for further analytics (e.g., to be analyze and process trends over time). In some examples, the reporter 212 can process and analyze trends over time based on the changes and/or comparisons of the performance indicator values over time and include such trends in the report. For example, a report may help a hospital to call for corrective maintenance of the imaging system 100 based on the data. In some examples, the reporter 212 can transmit the report to a user via a user interface. In some examples, the reporter 212 can output a report in paper form. The reporter 212 can provide reports periodically or aperiodically and/or based on a trigger (e.g., a signal from a user interface or other device). In some examples, such as when the interface 200 receives the study alert 112 from the dosage monitoring device 110, the reporter 212 processes the study alert 112 to determine a data set identifier. In such examples, the reporter 212 access the data set from the results storage 208 to provide a report (e.g., parameter adjustments, settings adjustments, alerts, etc.) corresponding to a comparison of the data set to other achieved data set in the results storage 208. The reporter 212 may instruct the interface 200 to transmit the report to the dosage monitoring device 110 via the network 118. In some examples, the reporter 212 is one or more active dashboards that tracks performance indicators over time to predict system performance and/or future image device malfunctions.

While example implementations of the quality assurance system 120 of FIG. 1 are illustrated in conjunction with FIGS. 1 and 2, processes and/or devices illustrated in conjunction with FIGS. 1 and 2 may be combined, divided, re-arranged, omitted, eliminated and/or implemented in any other way. Further, the interface 200, the processor 202, the timer/counter 204, the alert trigger 206, the results storage 208, the criteria storage 210, the reporter 212, and/or, more generally, the quality assurance system 120 of FIG. 2 may be implemented by hardware, machine readable instructions, software, firmware and/or any combination of hardware, machine readable instructions, software and/or firmware. Thus, for example, any of the interface 200, the processor 202, the timer/counter 204, the alert trigger 206, the results storage 208, the criteria storage 210, the reporter 212, and/or, more generally, the quality assurance system 120 of FIG. 2 can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the interface 200, the processor 202, the timer/counter 204, the alert trigger 206, the results storage 208, the criteria storage 210, the reporter 212, and/or, more generally, the quality assurance system 120 of FIG. 2 is/are hereby expressly defined to include a tangible computer readable storage device or storage disk such as a memory, a digital versatile disk (DVD), a compact disk (CD), a Blu-ray disk, etc. storing the software and/or firmware. Further still, the quality assurance system 120 of FIG. 2 include elements, processes and/or devices in addition to, or instead of, those illustrated in conjunction with FIG. 2, and/or may include more than one of any or all of the illustrated elements, processes and devices.

Flowcharts representative of example machine readable instructions for implementing the quality assurance system 120 of FIGS. 1 and/or 2 are shown in conjunction with FIGS. 3-6. Further, although the example program is described with reference to the flowcharts illustrated in conjunction with FIGS. 3-6, many other methods of implementing the quality assurance system 120 of FIGS. 1 and/or 2 may alternatively be used. For example, the order of execution of the blocks may be changed, and/or some of the blocks described may be changed, eliminated, or combined. Although the flowcharts of FIGS. 3-6 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of FIGS. 3-6 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 3-6 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 3:
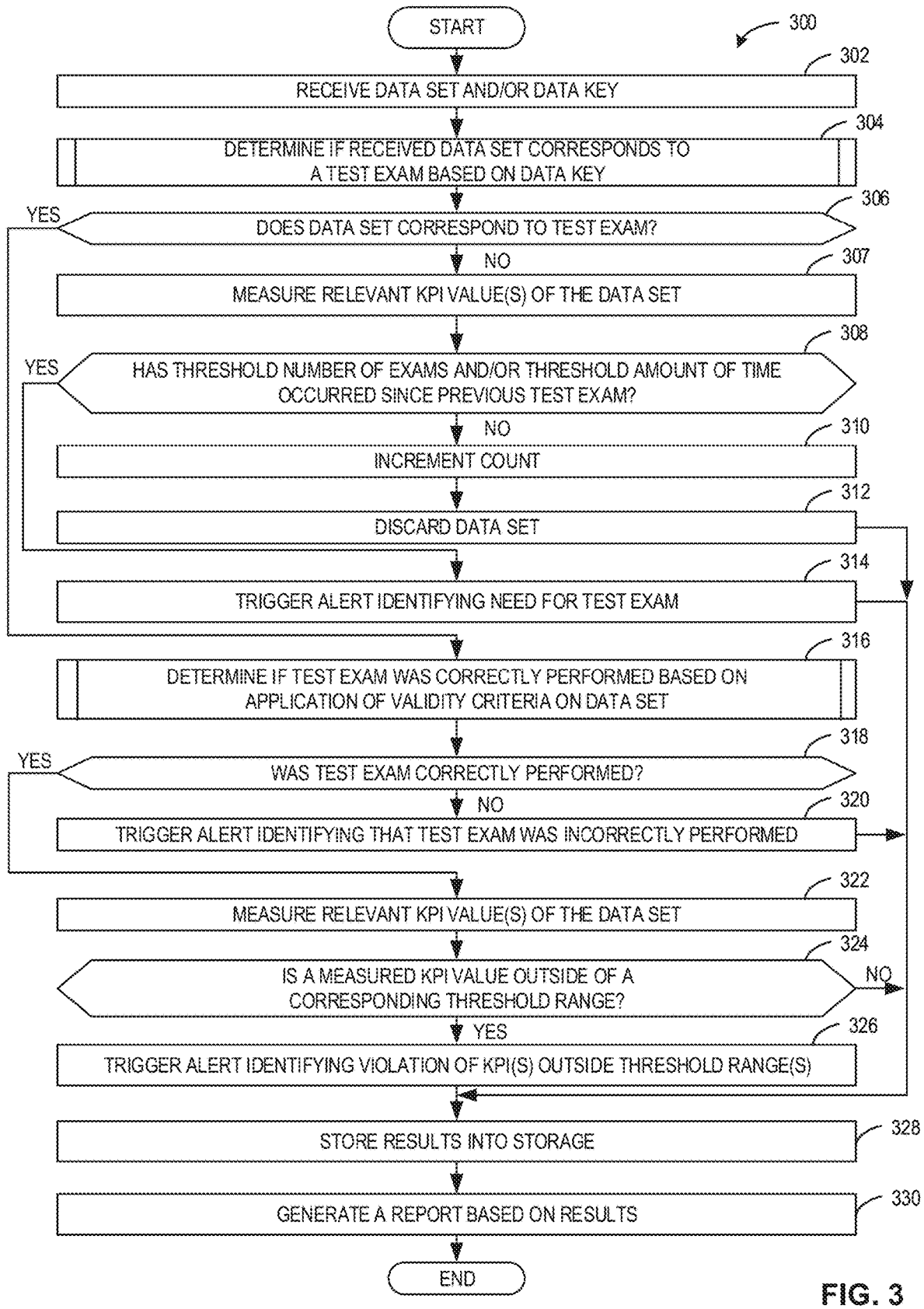
FIGS. 3-6 are flowcharts representative of example machine readable instructions that can be executed to implement the example quality assurance system of FIG. 2 to automatically assess quality of imaging systems.

FIG. 3 is a flowchart 300 representative of example machine readable instructions that can be executed by the quality assurance system 120 of FIG. 2 to automatically assess quality of imaging systems. Although the example flowchart of FIG. 3 is described in conjunction with a test exam of a phantom, the example flowchart of FIG. 3 may be utilized in conjunction with data from real patient data, filter ages, maintenance management systems (e.g., CMMS), etc.

At block 302, the imaging system 100 receives the data set 108 and/or data key 116. As described above in conjunction with FIG. 1, the data set 108 includes one or more images (e.g., an X-ray image(s), an MIll image, etc.) of the exposed subject along with metadata corresponding to an identifier and/or a phantom type and the data key 116 includes information corresponding to how to process the metadata to determine if the data set 108 corresponds to a test exam rather than an actual patient exam image(s). At block 304, the processor 202 determines if the received data set 108 corresponds to a test exam, rather than a patient exam, based on the data key 116, as further described below in conjunction with FIG. 4.

At block 306, the processor 202 determines if the data set 108 corresponds to a test exam. If the processor 202 determines that the data set 108 corresponds to a test exam (block 306: YES), the process continues to block 316. If the processor 202 determines that the data set 108 does not correspond to a test exam (block 306: NO) but instead corresponds to one or more images of a real patient anatomy, the processor 202 measures the relevant KPI value(s) of the data set (block 307). For example, if the data set 108 may correspond to an x-ray image of a real patient. In such an example, the quality assurance system 120 may select the x-ray image of the data set 108 to process a deviation index (e.g., a relevant performance indicator). As described above, a deviation index is a difference between an exposure index (e.g., a measure of the detector response to radiation in the relevant image region acquired with a digital x-ray imaging system as defined) and a target index (e.g., an expected exposure index when the detector is properly exposed, which can be disease dependent and fixed on a machine), thereby utilizing an automatic exposure control with patient specific data. In this manner, the quality assurance system 120 can track the DI as a function of disease, patient characteristics, etc., to determine the performance of the imaging device 100.

At block 308, the timer/counter 204 determines if a threshold number of exams and/or a threshold amount of time has not occurred since the previous test exam. For example, there may be a predefined condition requiring that a test exam must be performed after fifteen patient exams. Accordingly, the timer/counter 204 tracks the number of exams between a test exam to ensure that such a predefined condition is satisfied. If the timer/counter 204 determines that the threshold number of exams and/or the threshold amount of time has occurred since the previous test exam (block 308: NO), the timer/counter 204 increments the count (block 310) (e.g., to continue to track the number of patient exams being performed before a test exam is required, due to a predefined condition). Alternatively, as described above in conjunction with FIG. 2, if the timer/counter 204 corresponds to a threshold amount of time, block 310 can be eliminated and the timer/counter 204 continues to track time until the threshold amount of time elapses and/or a predefined point in time has been passed. For example, a predefined condition may require that a test exam occurs every 24 hours. In such an example, the timer/counter 204 tracks time to ensure that such a predefined condition is satisfied). At block 312, the processor 202 discards the data set 312 (other than relevant KPI values(s) that may have been measured at block 307).

If the timer/counter 204 determines that the threshold number of exams and/or the threshold amount of time has occurred since the previous test exam (block 308: YES), the alert trigger 206 triggers an alert identifying that a test exam is needed (block 314). As described above, such an alert may help ensure that predefined condition(s) are being satisfied. The alert can be transmitted to the hospital, the radiology department, the imaging system 100, the hospital information system 114, and/or a regulator committee to identify that a test exam is needed to verify that the functionality of the imaging system 100 is proper.

If the processor 202 determines that the data set 108 corresponds to a test exam (block 306: YES) rather than a patient exam, the processor 202 determines if the test exam was correctly performed based on application of validity criteria on the data set 108 (block 316), as further described below in conjunction with FIG. 5. At block 318, the processor 202 determines if the test exam was correctly performed. If the processor 202 determines that the test exam was not correctly performed (block 318: NO), the alert trigger 206 triggers an alert identifying that the test exam was incorrectly performed (block 320). The alert can be transmitted to the hospital, the radiology department, the imaging system 100, the hospital information system 114, etc., to identify that a test exam was incorrectly performed.

If the processor 202 determines that the test exam was correctly performed (block 318: YES), the processor 202 measures relevant performance indicator(s) of the data set (block 322). The relevant performance indicator(s) are stored in the criteria storage 210. In some examples, specific performance indicator(s) can be used for different phantom types. As described above in conjunction with FIG. 1, a performance indicator can be based on, for example, computed tomography numbers, noise, uniformity, tube current modulation, etc. At block 324, the processor 202 determines if one or more of the measured performance indicator values are outside of one or more corresponding threshold ranges. If the processor 202 determines that one or more measured performance indicator values are not outside of the one or more corresponding threshold ranges (block 324: NO), the process continues to block 328.

If the processor 202 determines that one or more measured performance indicator values are outside of the one or more corresponding threshold ranges (block 324: YES), the alert trigger 206 triggers an alert identifying violation of the one or more performance indicators outside of the one or more corresponding threshold ranges (block 326). The alert can be transmitted to the hospital, the radiology department, the imaging system 100, the hospital information system 114, etc., to identify that the performance of the imaging system 100 is unacceptable. At block 328, the processor 202 stores the results into the results storage 208. For example, the processor 202 can store the alerts, information corresponding to the alerts, performance indicator measurement(s), a count, a timestamp of the received data set 108, whether the data set was discarded or not, whether the test exam was performed correctly or not, and/or any other details related to the analysis of the received data set 108. At block 330, the reporter 212 provides a report based on the results. In some examples, the reporter 212 provides a report automatically (e.g., based on predefined points in time, other trigger, etc.) and/or based on instructions from a user. For example, the quality assurance system 120 can include a user interface to receive instructions corresponding to a report. The report can be customizable to gather data stored in the results storage 208 based on user preferences. For example, the reporter 212 can provide a report based on the performance indicator values of one or more imaging systems within a defined duration of time.

Figure 4:
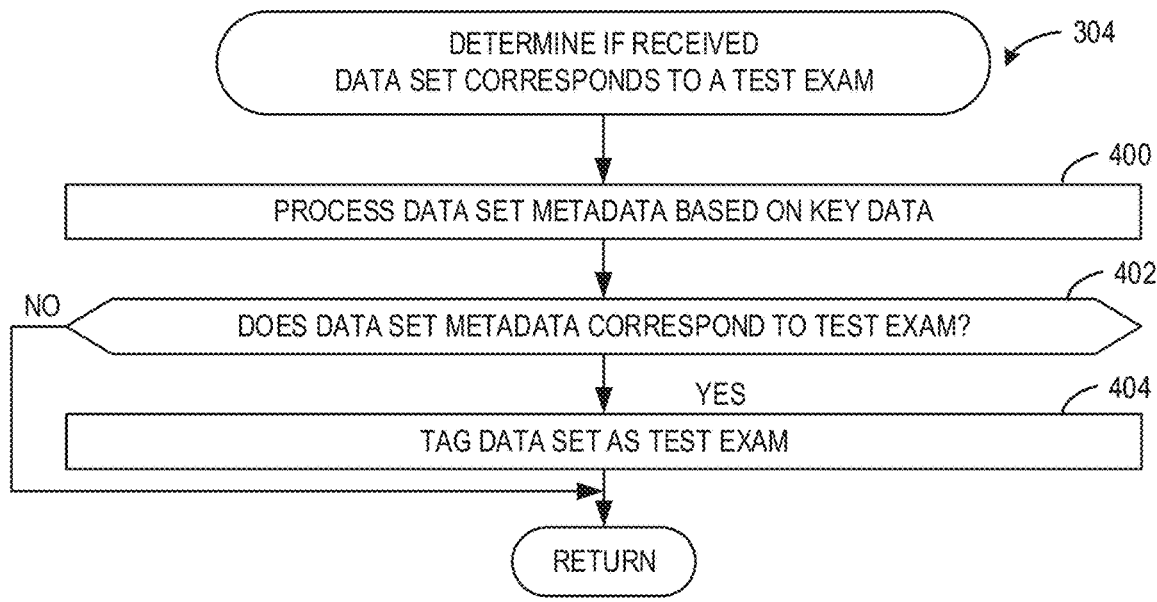

FIG. 4 illustrates a flowchart 304 representative of example machine readable instructions that can be executed by the quality assurance system 120 of FIG. 2 to determine if a received data set 108 corresponds to a test exam, as described above in conjunction with block 304 of FIG. 3. Although the example flowchart of FIG. 4 is described in conjunction with a test exam of a phantom, the example flowchart of FIG. 4 may be utilized in conjunction with data from real patient data, filter ages, maintenance management systems (e.g., CMMS), etc.

At block 400, the processor 202 processes the data set metadata (e.g., a DICOM header, etc.) based on the data key 116. For example, if the data key 116 identifies an identifier that corresponds to a test exam, the processor 202 processes the data set metadata to determine if the metadata includes the test exam identifier. For example, the data key 116 may include information that identifies that the data set 108 corresponds to a test exam, rather than a patient exam, when the header of the data set 108 includes an identifier of '0111' in an identifier frame. In some examples, the data key 116 may include a location of the identifier frame within the metadata. In such examples, the data processor 202 determines if the data set 108 corresponds to a test exam based on the information in the data key 116.

At block 402, the processor 202 determines if the data set metadata corresponds to a test exam. Using the above examples, if the processor 202 finds the test exam identifier in the metadata, the processor 202 determines that the data set 108 corresponds to a test exam. For example, the processor 202 processes the header of the data set 108 to locate the identifier frame. In such an example, if the processor 202 determines that the identifier frame includes the identifier '0111', the processor 202 determines that the data set 108 corresponds to a test exam, otherwise the processor 202 determines that the data set 108 corresponds to a patient test. If the processor 202 determines that the data set metadata does not correspond to a test exam (block 402: NO), the process returns to block 306 of FIG. 3. If the processor 202 determines that the data set metadata corresponds to a test exam (block 402: YES), the processor 202 tags the data set as corresponding to the test exam (block 404).

Figure 5:
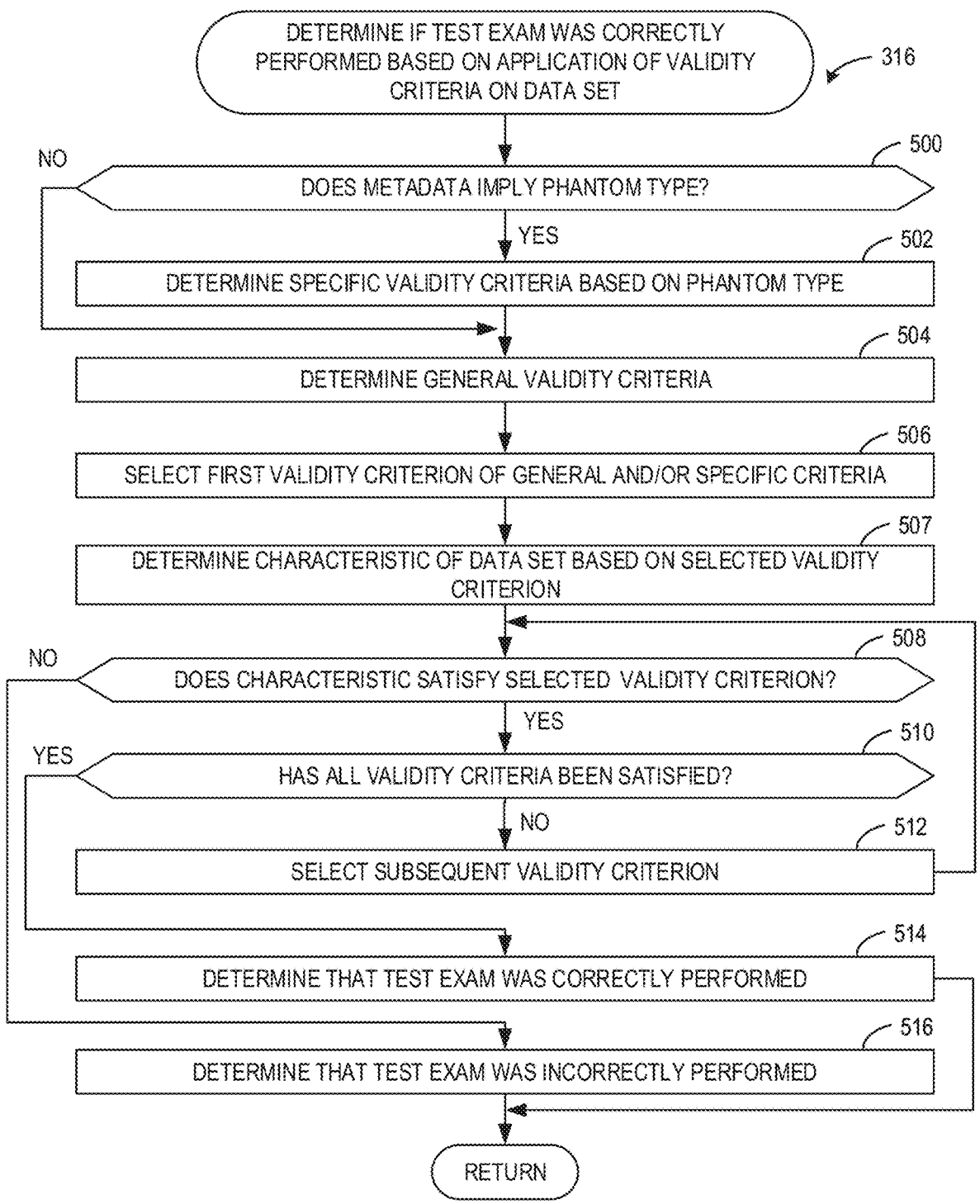

FIG. 5 is a flowchart 316 representative of example machine readable instructions that can be executed by the quality assurance system 120 of FIG. 2 to determine if test exam was correctly performed based on application of validity criteria on the data set 108, as described above in conjunction with block 316 of FIG. 3. Although the example flowchart of FIG. 5 is described in conjunction with a test exam of a phantom, the example flowchart of FIG. 5 may be utilized in conjunction with data from real patient data, filter ages, maintenance management systems (e.g., CMMS), etc.

At block 500, the processor 202 determines if the metadata implies a phantom type. For example, a technician can identify phantom type during a test exam and/or the hospital information system 100 may track phantoms used for test exams. In some examples, the imaging device 100 may correspond to a particular phantom type. For example, if the imaging system 100 is dedicated to mammography, a test exam corresponding to the data set 108 will correspond to mammography phantom types. In some examples, the imaging system 100 can include the phantom type in the data set metadata and/or the hospital information system 100 includes the phantom type in the data key 116. Additionally or alternatively, the hospital information system 114 can include instructions in the data key 116 corresponding to how to process the data set 108 to identify the phantom type. Accordingly, the processor 202 can determine how to process the metadata to determine the phantom type based on the information provided in the data key 116.

If the processor 202 determines that the metadata identifies a phantom type (block 500: YES), the processor 202 determines specific validity criteria based on phantom type (block 502). As described above in conjunction with FIG. 1, validity criteria may correspond to characteristic(s) of the data set 108, including a shift from an isocenter, differences in the levels of grey between two sides of the image, field uniformity values, AEC values, consistency of Hounsfield units, a tube current modulation, etc. For example, if the processor 202 determines that the data set 108 corresponds to a bone density spine phantom type, the data set 108 may identify a first difference in the levels of grey between the two sides of the phantom. In such an example, if the processor 202 determines that the data set 108 corresponds to a nuclear medicine thyroid phantom type, the data set 108 may identify a second difference in the levels of grey between the two sides of the phantom. The specific validity criteria corresponding to specific phantom types is stored in the criteria storage 210. Accordingly, when the image processor 202 determines that the data set 108 corresponds to a specific phantom type, the image processor 202 accesses the criteria storage 210 to determine the specific validity criteria corresponding to the phantom type.

At block 504, the processor 202 determines general validity criteria (e.g., validity criteria corresponding to any phantom type, etc.). In some examples, if the general validity criteria and the specific criteria are opposing, the processor 202 discards the opposing general validity criteria (e.g., in favor of the specific validity criteria) while maintaining any remaining (e.g., no-overridden) elements of the general criteria. For example, if the general validity criteria may correspond to a first shift from an isocenter of the image. However, a specific phantom type (e.g., a mammography quality phantom) may correspond to a second shift from an isocenter different than then the first shift from the isocenter of the image. Accordingly, if the processor 202 determines that the phantom corresponds to a mammography quality phantom, for example, the processor 202 processes the data set 108 based on the second shift and discards the first shift.

At block 506, the processor 202 selects a first validity criterion from the determined general and/or specific criteria. At block 508, the processor 202 determines if the data set 108 satisfies the selected validity criterion. For example, if the validity criterion corresponds to a predefined set of acceptable AEC values, the processor 202 determines the AEC value of the data set 108 and compares the determined AEC value to the predefined set of AEC values. If the determined AEC value of the data set 108 is within the predefined set of AEC values, the processor 202 determines that the data set 108 satisfies the selected validity criterion, otherwise the processor 202 determines that the data set 108 does not satisfy the selected validity criterion.

If the processor 202 determines that the data set 108 does not satisfy the validity criterion (block 508: NO), the processor 202 determines that the test exam was incorrectly performed (block 516). If the processor 202 determines that the data set 108 satisfies the validity criterion (block 508: YES), the processor 202 determines if all validity criteria have been satisfied (block 510). For example, if there are four different validity criteria to be satisfied, and only two criteria have been tested, the process returns to block 510 to process the data set 108 based on the two remaining criteria. If the processor 202 determines that all validity criteria have not been satisfied (block 510: NO), the processor 202 selects a subsequent validity criterion (block 512) and the process returns to block 508 until all the criteria have been analyzed. If the processor 202 determines that all validity criteria have been satisfied (block 510: YES), the processor 202 determines that the test exam was correctly performed (block 514).

Figure 6:
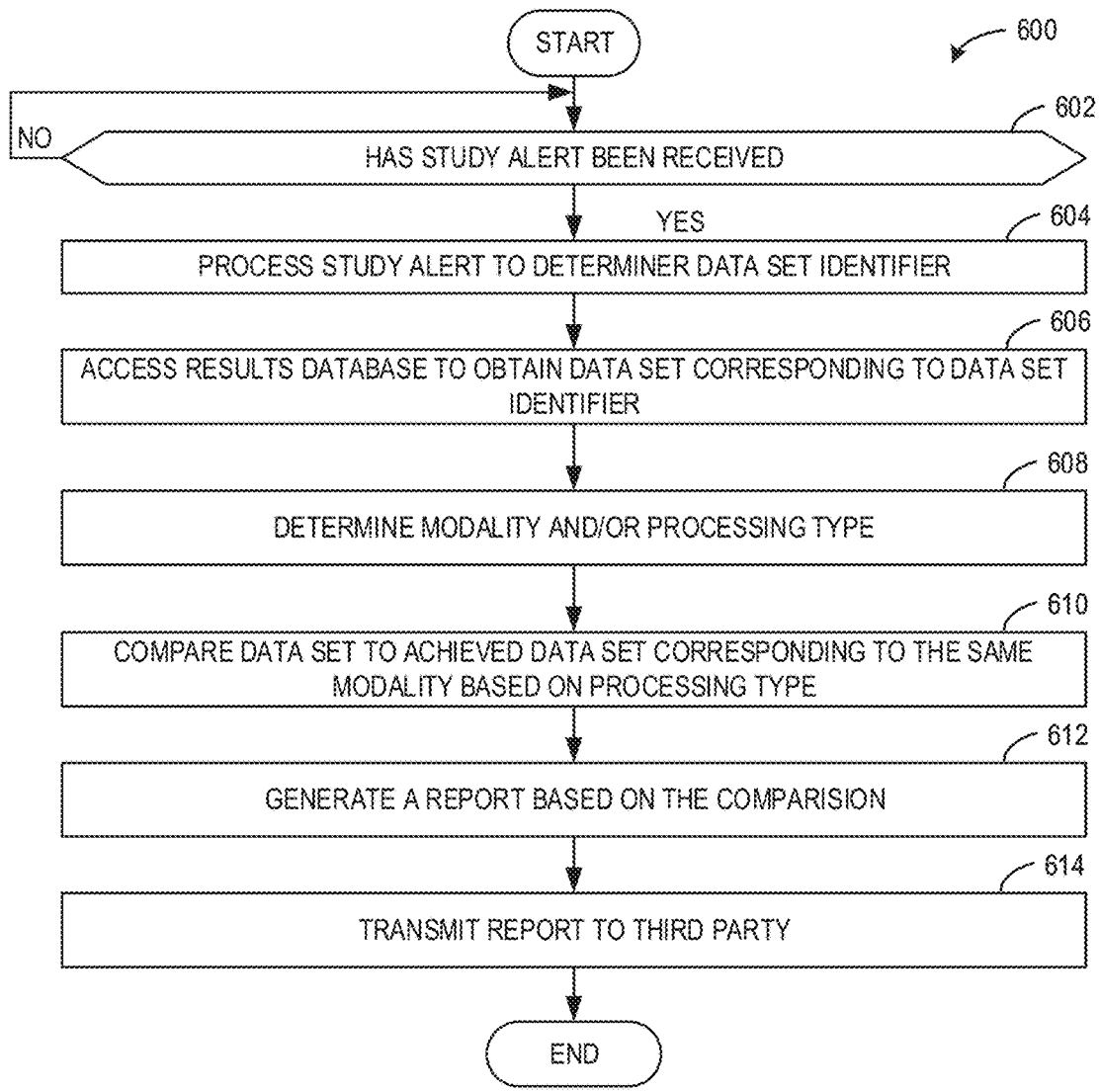

FIG. 6 is a flowchart 600 representative of example machine readable instructions that can be executed by the quality assurance system 120 of FIG. 2 to process the example study alert 112 of FIG. 1.

At block 602, the interface 200 determines if the example study alert has been received. As described above in conjunction with FIG. 1, the dosage monitoring device 110 generate the study alert 112 corresponding to a particular data set based on predefined criteria. For example, quality assurance system 120 generate the study alert 112 to notify a user that an exam was performed on one or more patients while the corresponding modality did not successfully pass the daily QA test. At block 604, the reporter 212 processes the study alert 112 to determine the data set identifier embedded in the study alert 112. At block 606, the reporter 212 assesses the result storage 208 to obtain the data set correspond to the data set identifier. Additionally, the reporter 212 may obtain data related to the processing of the data set.

At block 608, the reporter 212 determines the modality and/or processing type. The modality, for example, may correspond to the data set 108 itself (e.g., does the data set 108 correspond to a mammography image, a CT image, an MRI, etc.). The processing type can be defined in received study alert 112. The processing type defines how what characteristics to compare. For example, the processing type may correspond to field uniformity, AEC, phantom centering, consistency of HUs, tube current modulation, etc. At block 610, the reporter 212 compares the data set to achieved data set (e.g., in the result storage 208) corresponding to the same modularity based on the processing type. At block 612, the reporter 212 provides a report based on the comparison. For example, the reporter 212 may provide comparison results, alerts based on the comparison, etc. At block 614, the interface 200 transmits the report to a third party (e.g., an operator, a device, etc.). Accordingly, the dose monitoring device 100 can adjust parameters to try to adjust settings of the imaging device 100 and/or trigger alerts to notify an operator of an issue, for example.

Figure 7:
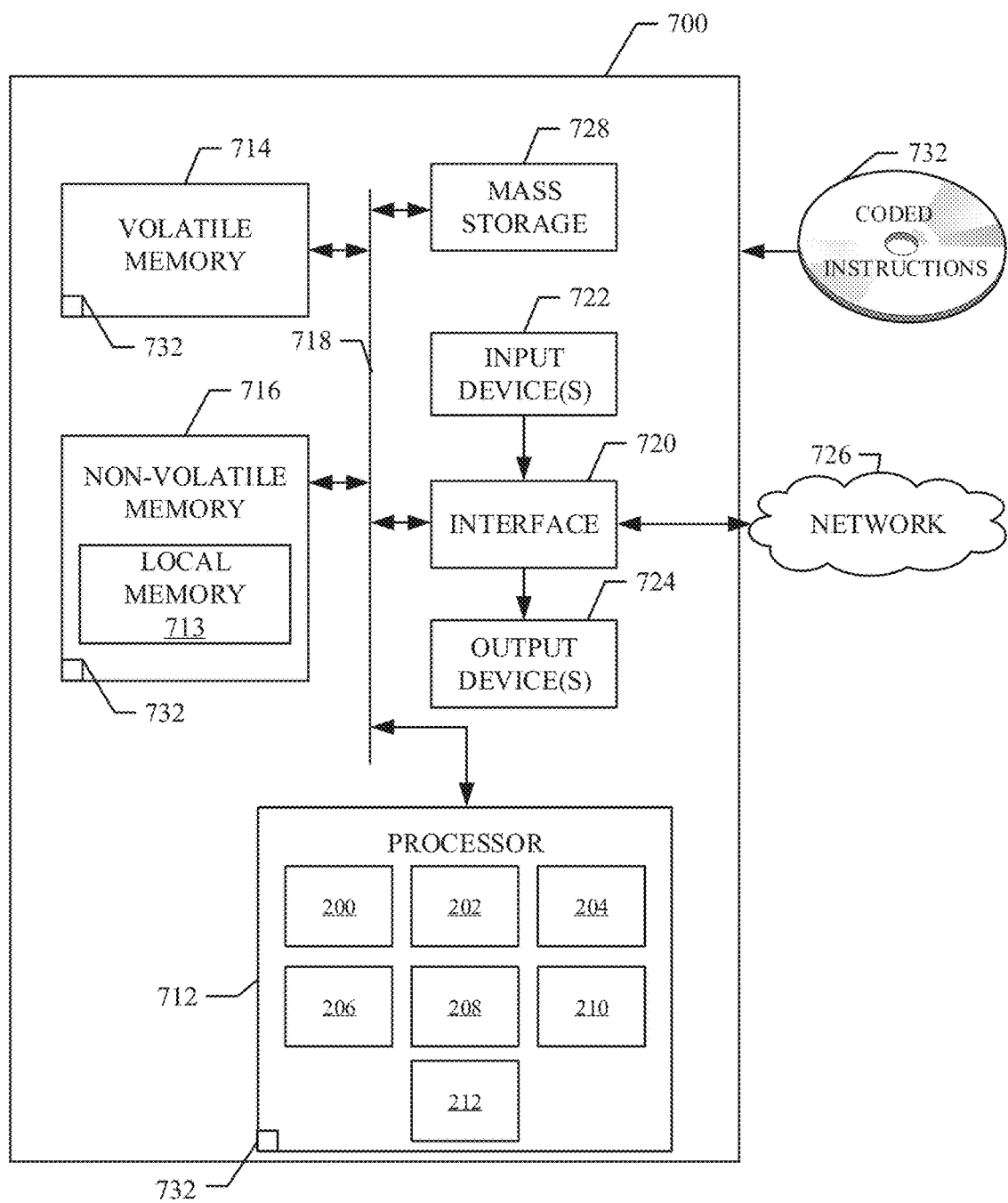
FIG. 7 is a block diagram of a processing system structured to execute the example machine readable instructions of FIGS. 3-6 to implement the example quality assurance system of FIG. 2.

FIG. 7 is a block diagram of an example processor platform 700 structured to executing the instructions of FIG. 7 to implement the quality assurance system 120 of FIGS. 1 and/or 2. The processor platform 700 can be, for example, a server, a personal computer, a mobile device (e.g., a cell phone, a smart phone, a tablet such as an iPad™), a personal digital assistant (PDA), an Internet appliance, or any other type of computing device.

The processor platform 700 of the illustrated example includes a processor 712. The processor 712 of the illustrated example is hardware. For example, the processor 712 can be implemented by integrated circuits, logic circuits, microprocessors or controllers from any desired family or manufacturer.

In the examples, the machine readable instructions include a program for execution by one or more processors such as the processor 712 shown in the example processor platform 700 discussed below in connection with FIG. 7. The machine readable instructions may be stored on a tangible computer readable storage medium such as a CD-ROM, a floppy disk, a hard drive, a digital versatile disk (DVD), a Blu-ray disk, or a memory associated with the processor 712, but the entire program and/or parts thereof could alternatively be executed by a device other than the processor 712 and/or embodied in firmware or dedicated hardware.

The processor 712 of the illustrated example includes a local memory 713 (e.g., a cache). The example processor 712 of FIG. 7 executes the instructions of FIGS. 3-6 to implement the interface 200, the processor 202, the timer/counter 204, the alert trigger 206, the results storage 208, the criteria storage 210, and/or the reporter 212.

The processor 712 of the illustrated example is in communication with a main memory including a volatile memory 714 and a non-volatile memory 716 via a bus 718. The volatile memory 714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 716 may be implemented by flash memory and/or any other desired type of memory device. Access to the main memory 714, 716 is controlled by a clock controller.

The processor platform 700 of the illustrated example also includes an interface circuit 720. The interface circuit 720 may be implemented by any type of interface standard, such as an Ethernet interface, a universal serial bus (USB), and/or a PCI express interface.

In the illustrated example, one or more input devices 722 are connected to the interface circuit 720. The input device(s) 722 permit(s) a user to enter data and commands into the processor 712. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 724 are also connected to the interface circuit 720 of the illustrated example. The output devices 724 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 720 of the illustrated example, thus, typically includes a graphics driver card, a graphics driver chip or a graphics driver processor.

The interface circuit 720 of the illustrated example also includes a communication device such as a transmitter, a receiver, a transceiver, a modem and/or network interface card to facilitate exchange of data with external machines (e.g., computing devices of any kind) via a network 726 (e.g., an Ethernet connection, a digital subscriber line (DSL), a telephone line, coaxial cable, a cellular telephone system, etc.).

The processor platform 700 of the illustrated example also includes one or more mass storage devices 728 for storing software and/or data. Examples of such mass storage devices 728 include floppy disk drives, hard drive disks, compact disk drives, Blu-ray disk drives, RAID systems, and digital versatile disk (DVD) drives.

The coded instructions 732 of FIG. 3-6 may be stored in the mass storage device 728, in the volatile memory 714, in the non-volatile memory 716, and/or on a removable tangible computer readable storage medium such as a CD or DVD.

From the foregoing, it will be appreciated that the above disclosed methods, apparatus, and articles of manufacture have been disclosed for automatically assessing quality of imaging systems. In the field of medical imaging, conventional techniques of measuring imaging system performance include performing test exams are whose results are analyzed by a technician/physicist in the hospital and/or are outsourced to determine if the performance of the imaging device is acceptable (e.g., based on key performance indicators (KPIs)). However, such analyzation is expensive and measurements are not stored anywhere to observe trends over time. Additionally, the list of key performance indicator is not shared between hospitals using the same device. Accordingly, there is no traceability in a database (e.g., among KPIs and/or for the same KPI across multiple imaging devices and/or hospitals) and no way to observe evolutions in performance indicators over time. Additionally, there is no automatic notification to a hospital that a particular performance indicator is outside of a predefined limit or if a test exam is needed (e.g., a test exam hasn't been performed within a preset amount of time/number of scans).

Examples disclosed herein include an integrated system that solves the above problems by implementing an integrated system in a hospital information system that automatically analyzes test exams and stores results to provide reports based on imaging device functionality over time. Examples disclosed herein include gather scanning data set and (A) identify if the data set correspond to test exams, (B) determine the validity of the test exams, and (C) determine functionality of the scanning device based on measured performance indicators on the validated data set to provide more complete information corresponding to scanning devices (e.g., trends over time, etc.) and eliminate the costs associated with daily device manually analyzing test exam images.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
    a processor configured to:
        determine whether received data from an imaging device corresponds to a test exam;
        in response to determining that the received data corresponds to the test exam, determine whether the test exam was correctly performed based on a comparison of the data to a validity criterion; and
        when the test exam was correctly performed, determine that the imaging device satisfies a performance criteria based on a comparison of a characteristic of the data corresponding to a performance indicator with a performance threshold;
    a storage configured to store the performance indicator in conjunction with the data; and
    a reporter configured to generate a report including the performance indicator and the data, the report including a comparison of the performance indicator with respect to time.

2. The apparatus of claim 1, wherein the data is generated by a first imaging device, wherein the report includes a second performance indicator corresponding to a second data from a second imaging device.

3. The apparatus of claim 2, wherein the processor is to select the first and second performance indicators as being relevant based on at least one of (A) relating to imaging or (B) relating to possible malfunctions.

4. The apparatus of claim 1, wherein the reporter is to analyze trends with respect to time based on the comparison.

5. The apparatus of claim 4, wherein the reporter develops an active dashboard to track the performance indicator over time.

6. The apparatus of claim 1, further including an alert trigger configured to generate an alert identifying at least one of (A) the test exam not being correctly performed or (B) the performance indicator being outside a threshold range.

7. An apparatus comprising:
    a processor configured to:
        determine whether received data from an imaging device corresponds to a test exam;
        in response to determining that the received data corresponds to the test exam, determine whether the test exam was correctly performed based on a comparison of the data to a validity criterion; and when the test exam was correctly performed, determine that the imaging device satisfies a performance criteria based on a comparison of a characteristic of the data corresponding to a performance indicator with a performance threshold;
a storage configured to store the performance indicator in conjunction with the data;
a timer configured to monitor an amount of time from when previous received data corresponded to the test exam; and
an alert trigger configured to generate an alert when the amount of time from when the previous received data corresponding to the test exam exceeds a threshold, the alert identifying that the imaging device may be faulty.

8. The apparatus of claim 1, further including:
a counter configured to monitor a number of scans from when the previous received data corresponded to the test exam; and
an alert trigger configured to generate an alert when the number of scans from when the previous received data corresponding to the test exam exceeds a threshold, the alert identifying that the imaging device may be faulty.

9. An apparatus comprising:
a processor configured to:
determine whether received data from an imaging device corresponds to a test exam by processing metadata of the data to determine if a test exam identifier is present in the metadata;
in response to determining that the received data corresponds to the test exam, determine whether the test exam was correctly performed based on a comparison of the data to a validity criterion; and
when the test exam was correctly performed, determine that the imaging device satisfies a performance criteria based on a comparison of a characteristic of the data corresponding to a performance indicator with a performance threshold; and
a storage configured to store the performance indicator in conjunction with the data.

10. The apparatus of claim 9, further including an interface to receive a data key from a hospital information system, the key data including at least one of the test exam identifier or a location of an identifier frame in the metadata.

11. The apparatus of claim 1, wherein the processor is configured to determine if the test exam was correctly performed by:
obtaining the validity criterion corresponding to the data from storage, the validity criterion corresponding to the characteristic;
determining the characteristic of the data; and
determining the test exam was correctly performed when the determined characteristic satisfies the validity criterion.

12. The apparatus of claim 1, wherein the processor is configured to determine that the imaging device satisfies the performance indicator by determining the characteristic of the data corresponding to the performance indicator and comparing the characteristic to a threshold defined by the performance indicator.

13. The apparatus of claim 1, wherein the processor is to, in response to determining that the received data corresponds to patient data, determine that the imaging device satisfies a second performance criteria based on a comparison of a second characteristic of second data corresponding to the second performance indicator with a second performance threshold.

14. A method comprising:
determining whether received data from an imaging device corresponds to a test exam;
in response to determining that the received data corresponds to the test exam, determining whether the test exam was correctly performed based on a comparison of the data to a validity criterion;
when the test exam was correctly performed, determining that the imaging device satisfies a performance criteria based on a comparison of a characteristic of the data corresponding to a performance indicator to the data with a performance threshold;
storing the performance indicator in conjunction with the data; and
generating a report including the performance indicator and the data, the report including a comparison of the performance indicator with respect to time.

15. The method of claim 14, wherein the data is generated by a first imaging device, wherein the report includes a second performance indicator corresponding to a second data from a second imaging device.

16. The method of claim 14, further including generating an alert based on at least one of (A) the test exam not being correctly performed or (B) the performance indicator being outside a threshold range.

17. A method comprising:
determining whether received data from an imaging device corresponds to a test exam;
in response to determining that the received data corresponds to the test exam, determining whether the test exam was correctly performed based on a comparison of the data to a validity criterion;
when the test exam was correctly performed, determining that the imaging device satisfies a performance criteria based on a comparison of a characteristic of the data corresponding to a performance indicator to the data with a performance threshold;
storing the performance indicator in conjunction with the data;
monitoring an amount of time from when previous received data corresponded to the test exam; and
generating an alert when the amount of time from when the previous received data corresponding to the test exam exceeds a threshold.

18. A tangible computer readable storage medium comprising instructions which, when executed, cause a machine to at least:
determine whether received data from an imaging device corresponds to a test exam;
in response to determining that the received data corresponds to the test exam, determine whether the test exam was correctly performed based on a comparison of the data to a validity criterion;
when the test exam was correctly performed, determine that the imaging device satisfies a performance criteria based on a comparison of the data to a performance indicator with a performance threshold;
storing the performance indicator in conjunction with the data; and
generate a report including the performance indicator and the data, the report including a comparison of the performance indicator with respect to time.

19. The computer readable storage medium of claim 18, wherein the data is generated by a first imaging device, wherein the report includes a second performance indicator corresponding to a second data from a second imaging device.

20. The computer readable storage medium of claim 19, wherein the instructions cause the machine to select the first and second performance indicators as being relevant based on at least one of (A) relating to imaging or (B) relating to possible malfunctions.

* * * * *